United States Patent
Yamamoto et al.

(10) Patent No.: US 9,131,666 B2
(45) Date of Patent: Sep. 15, 2015

(54) HATCHING EGG INSPECTION APPARATUS

(75) Inventors: Mitsuo Yamamoto, Kameoka (JP);
Tsuyoshi Yamamoto, Kameoka (JP);
Shinichi Fujitani, Kyoto (JP);
Takatsugu Tahara, Kyoto (JP); Toyoaki Ohashi, Kyoto (JP)

(73) Assignees: Yamamoto Corp., Kyoto (JP); Nabel Co., Ltd., Kyoto (JP)

( * ) Notice: Subject to any disclaimer, the term of this patent is extended or adjusted under 35 U.S.C. 154(b) by 0 days.

(21) Appl. No.: 14/400,488

(22) PCT Filed: May 18, 2012

(86) PCT No.: PCT/JP2012/062757
§ 371 (c)(1),
(2), (4) Date: Nov. 11, 2014

(87) PCT Pub. No.: WO2013/171890
PCT Pub. Date: Nov. 21, 2013

(65) Prior Publication Data
US 2015/0138537 A1 May 21, 2015

(51) Int. Cl.
*A01K 43/00* (2006.01)
*G01N 33/08* (2006.01)
(Continued)

(52) U.S. Cl.
CPC .............. *A01K 43/00* (2013.01); *G01N 21/49* (2013.01); *G01N 21/59* (2013.01); *G01N 33/085* (2013.01)

(58) Field of Classification Search
CPC ..... G01N 33/085; G01N 33/08; A01K 43/00; A01K 45/007; C12N 7/00
USPC ........................................................ 356/53
See application file for complete search history.

(56) References Cited

U.S. PATENT DOCUMENTS

| 3,616,262 | A  | * | 10/1971 | Coady et al. ............... 435/286.4 |
| 5,017,003 | A  |   | 5/1991  | Keromnes et al. |
| 5,277,320 | A  | * | 1/1994  | Corkill et al. .................. 209/511 |
| 6,357,140 | B1 | * | 3/2002  | Heyer et al. ...................... 34/236 |

(Continued)

FOREIGN PATENT DOCUMENTS

| CN | 101566614 A | 10/2009 |
| CN | 101672839 A | 3/2010 |

(Continued)

OTHER PUBLICATIONS

International Search Report; PCT/JP2012/062757; Aug. 14, 2012.
(Continued)

*Primary Examiner* — Tarifur Chowdhury
*Assistant Examiner* — Md Rahman
(74) *Attorney, Agent, or Firm* — Studebaker & Brackett PC

(57) ABSTRACT

A hatching egg inspection apparatus includes a loader unit, an inspection unit for determining the viability or the like as to whether a hatching egg is an unfertilized egg or a growth-stopping egg, a rejection unit for rejecting a hatching egg determined to be an unfertilized egg or the like, and an unloader unit for sending a hatching egg toward the next step. The inspection unit is provided with a light emitting unit for emitting prescribed light toward the hatching egg, a cap attachment unit through which the light having been emitted to the hatching egg and having transmitted through the hatching egg passes, and a light receiving unit for receiving the light that has passed through the cap attachment unit. The cap attachment unit includes a cylindrical cap coming into contact with the hatching egg, and a plate to which the cap is attached.

9 Claims, 15 Drawing Sheets

(51) Int. Cl.
  *G01N 21/49* (2006.01)
  *G01N 21/59* (2006.01)

(56) References Cited

U.S. PATENT DOCUMENTS

| | | | |
|---|---|---|---|
| 6,373,560 | B1 | 4/2002 | Roux |
| 6,860,225 | B2 | 3/2005 | Hebrank |
| 2003/0156273 | A1* | 8/2003 | Kageyama et al. ............ 356/52 |
| 2004/0107912 | A1 | 6/2004 | Hebrank |
| 2009/0091743 | A1 | 4/2009 | Hebrank et al. |

FOREIGN PATENT DOCUMENTS

| | | |
|---|---|---|
| JP | 07-209209 A | 8/1995 |
| JP | 09-127096 A | 5/1997 |
| JP | 2001-208680 A | 8/2001 |
| JP | 2005-532046 A | 10/2005 |
| JP | 2011-106892 A | 6/2011 |
| JP | 2011-169629 A | 9/2011 |
| JP | 4858863 B2 | 1/2012 |
| JP | 2012-108040 A | 6/2012 |
| WO | 89/06797 A1 | 7/1989 |
| WO | 03/096028 A2 | 11/2003 |
| WO | 2009/044243 A2 | 4/2009 |

OTHER PUBLICATIONS

The first Office Action issued by the Chinese Patent Office on Jul. 21, 2015, which corresponds to Chinese Patent Application No. 201280073275.7 and is related to U.S. Appl. No. 14/400,488.

* cited by examiner

FIG.17
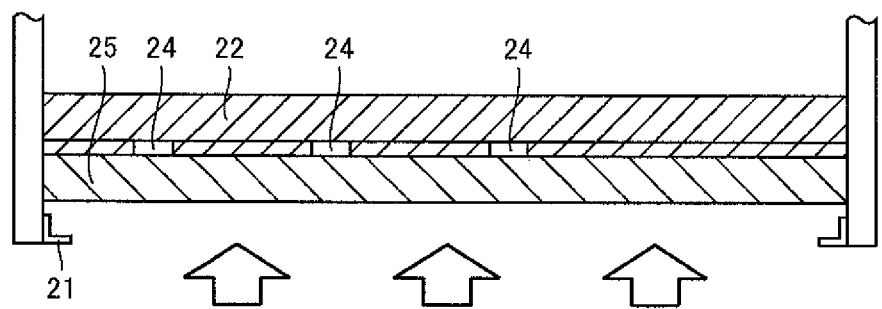
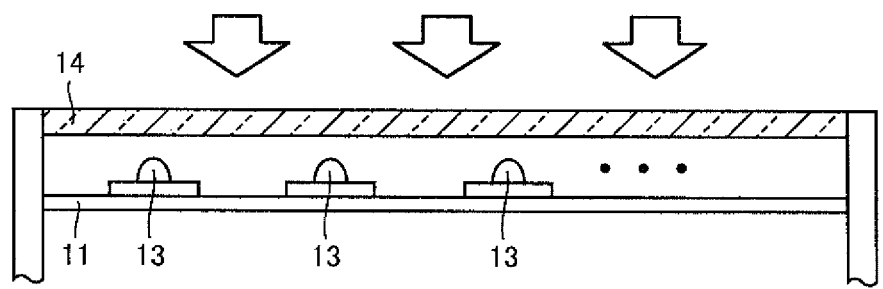

HATCHING EGG INSPECTION APPARATUS

TECHNICAL FIELD

The present invention relates to a hatching egg inspection apparatus, and particularly to a hatching egg inspection apparatus mainly for determining the viability or the like of a hatching egg.

BACKGROUND ART

Eggs typified by chicken eggs and the like include eggs for hatching chicks, in addition to table eggs. Such eggs are particularly referred to as "hatching eggs". When a hatching egg is incubated for prescribed days under certain environment such as a prescribed temperature, a chick hatches. In a hatchery where a large number of chicks are hatched, the production process is managed such that hatching eggs obtained within a certain period can hatch all together on the same prescribed day.

Inside a hatching egg, development of an embryo progresses from the point of egg laying. Therefore, first, in the step of accumulating hatching eggs obtained within a certain period, the hatching eggs are kept under the environment in which the temperature is equal to or lower than 28° C., to suppress the embryonic cell division and cause the hatching eggs to diapause. When the prescribed number of hatching eggs are accumulated, preliminary heating is performed to resume the activity of the resting embryos. The hatching eggs are inspected for grime or cracks, and are placed on a dedicated tray referred to as "setter tray". The hatching eggs housed in the setter tray are kept under the environment in which the temperature is 38° C., and thereby, the hatching eggs enter the incubation process. A date of starting the incubation process is defined as an incubation starting date, and the number of days elapsed from the incubation starting date is defined as the number of incubation days. The chicks are born almost on day 21 of the number of incubation days.

On day 18 or 19 of the number of incubation days, the work of moving the hatching eggs from the setter tray to a dedicated tray referred to as "hatcher tray" is performed in preparation for incubation of the hatching eggs. When this work of moving is performed, a prescribed inspection is performed on the hatching eggs. The inspection will now be described.

Even for the hatching eggs, not all of the hatching eggs hatch, and the hatching eggs may include some unfertilized eggs at a certain rate from the beginning, or may include some growth-stopping eggs in which the growth of an embryo stops during the course of the incubation process. Some of these unfertilized eggs or growth-stopping eggs go rotten at the contents and the contents-rotten egg is called "spoiled egg". The rotten contents generate gas. When the gas is generated in a space closed by a shell, the pressure inside the egg becomes high, and thus, some of the spoiled eggs burst. The inventors describe such burst egg or an egg that may burst as "explosion egg".

When a hatching egg housed in the setter tray explodes (bursts), the rotten contents are scattered and miscellaneous bacteria included in the contents contaminate even the surrounding healthy hatching eggs. When the hatching egg explodes after movement to the hatcher tray, the already born chicks may be contaminated.

Even in the case of the spoiled egg that does not explode, the contaminated contents inside the egg may seep out to the surface of the egg due to the pressure of the gas generated in the egg. In this case as well, it is conceivable that transfer of the contents that have seeped out to the surface of the egg results in contamination of the surrounding healthy hatching eggs and the tray. Furthermore, when the hatching egg is vaccinated, the hatching egg having the increased inner pressure may explode due to the impact when an injection needle comes into contact with the shell.

In order to prevent such contamination, inspection is performed to divide the hatching eggs into healthily grown hatching eggs and unfertilized eggs, growth-stopping eggs or the like. Namely, the viability of the hatching eggs is determined. As proposed in, for example, PTD 1 (Japanese Patent Laying-Open No. 09-127096) or PTD 2 (WO 2009/044243), an optical method has been conventionally used to determine the viability of hatching eggs. According to this method, the viability is determined by emitting the prescribed light toward a hatching egg and analyzing a time-varying component of the light that has transmitted through the hatching egg. A hatching egg determined to be an unfertilized egg or a growth-stopping egg in this manner is removed immediately, which prevents the healthily grown hatching eggs from being contaminated.

CITATION LIST

Patent Document

PTD 1: Japanese Patent Laying-Open No. 09-127096
PTD 2: WO 2009/044243

SUMMARY OF INVENTION

Technical Problem

However, the conventional inspection method used to determine the viability of the hatching eggs has the following problem. As described above, the viability of the hatching eggs is determined by analyzing the component of the light that has transmitted through the hatching egg, and thus, it is necessary to block the light incident from outside the hatching egg. Therefore, an inspection apparatus used in this inspection is provided with a cap for blocking the light other than the light having transmitted through the inside of or diffused in the hatching egg. In determination of the viability, the cap is first brought into contact with the shell of the hatching egg, and next, the prescribed light is emitted toward the hatching egg in this state, and the light having passed through the cap is received by a light receiving element as the light having transmitted through the hatching egg. Next, the received light is analyzed as an electric signal. The viability of the hatching egg is thus determined.

As described above, the cap that comes into contact with the shell of the hatching egg is needed as the inspection apparatus to determine the viability based on the time-varying component of the light having transmitted through the hatching egg. Therefore, when the hatching egg to be inspected is a spoiled egg or particularly an explosion egg, the hatching egg may explode due to the contact with this cap. In order to prevent spreading of contamination into the other healthy hatching eggs caused by the cap or the like to which the miscellaneous bacteria or the like attach due to the explosion, the cap or the like must be cleaned and sterilized immediately. In addition, in the hatchery, many hatching eggs are treated, and thus, a plurality of hatching eggs on the setter tray are inspected simultaneously. Since a plurality of caps corresponding to the hatching eggs to be measured are present in the inspection apparatus, it is necessary to consider contamination of the plurality of caps at a time.

In order to hatch healthy and tough chicks, it is required not only to take measures against contamination caused by the explosion of the hatching egg but also to constantly keep hygienic the environment for hatching the hatching eggs. Particularly, in order to prevent cross infection, it is required to routinely sterilize a portion like the aforementioned cap that comes into contact with the hatching egg even when the portion is not contaminated by the explosion egg. Furthermore, in the hatchery where a large number of chicks are hatched, it is required to easily perform the maintenance work such as sterilization and replacement without hampering the productivity when the cap or the like is contaminated.

The present invention has been made as part of the aforementioned development and an object of the present invention is to provide a hatching egg inspection apparatus in which measures can be taken against contamination without hampering the productivity.

Solution to Problem

A hatching egg inspection apparatus according to the present invention is a hatching egg inspection apparatus for inspecting a plurality of hatching eggs each arranged at a prescribed position, including: a light emitting unit; a cap attachment unit; a light receiving unit; a light receiving unit protection unit; and a holding unit. The light emitting unit includes a light emitting element arranged to correspond to the prescribed position and emits prescribed light from the light emitting element toward each corresponding hatching egg. The cap attachment unit has: a cylindrical cap which is arranged to correspond to the prescribed position, which comes into contact with the hatching egg, and which allows the light having been emitted from the light emitting element and having transmitted through the inside of or diffused in the hatching egg to pass through; and a base to which the cap is attached. The light receiving unit includes a light receiving element for receiving the light that has passed through the cap attachment unit. The light receiving unit protection unit is arranged between the cap attachment and the light receiving unit to protect the light receiving unit. The holding unit detachably holds the cap attachment unit.

Another hatching egg inspection apparatus according to the present invention is a hatching egg inspection apparatus for inspecting a plurality of hatching eggs that allow light to transmit through, with the hatching eggs each arranged at a prescribed position, including: a light irradiation unit for emitting the light toward the hatching eggs; a plurality of light passing units each of which is arranged to correspond to the prescribed position, which allows only the light having transmitted through the inside of the hatching egg, of the light emitted from the light irradiation unit, to pass through, and which blocks the passing light from the other light; and a light receiving unit spaced apart from the light passing units and receiving the light having passed through each light passing unit. Each light passing unit includes a cap that comes into contact with the hatching egg and can be separated from the light receiving unit. The cap includes a first opening portion coming into contact with the hatching egg, a second opening portion spaced apart from the first opening portion, and a connecting portion interposed between the first and second opening portions. The first opening portion is formed to come into close contact with an outer surface of the hatching egg, and is formed such that the light having transmitted through the inside of the hatching egg is incident through the outer surface of the hatching egg. The connecting portion is formed such that the light incident from the first opening portion travels toward the second opening portion, and is formed to expand and contract in a direction substantially vertical to the first opening portion. The second opening portion is formed such that the light having passed through the connecting portion exits toward the light receiving unit.

Still another hatching egg inspection apparatus according to the present invention is a hatching egg inspection apparatus for inspecting a plurality of hatching eggs each arranged at a prescribed position, including: a light emitting unit; a cap attachment unit; a light receiving unit; and a holding unit. The light emitting unit emits prescribed light toward the hatching eggs. The cap attachment unit has: a cap which is arranged to correspond to the prescribed position, which comes into contact with the hatching egg, and which allows the light having been emitted from the light emitting element and having transmitted through the inside of or diffused in the hatching egg to pass through; and a base to which the cap is attached. The light receiving unit includes a light receiving element for receiving the light that has passed through the cap attachment unit via the cap. The holding unit detachably holds the cap attachment unit.

Advantageous Effects of Invention

According to the hatching egg inspection apparatus, another hatching egg inspection apparatus and still another hatching egg inspection apparatus of the present invention, measures can be taken against contamination for the hatching egg inspection apparatus without hampering the productivity.

BRIEF DESCRIPTION OF DRAWINGS

FIG. 17 is a side view including a partial cross section for describing a characteristic of the inspection unit in the embodiment.

DESCRIPTION OF EMBODIMENTS

Figure 1:
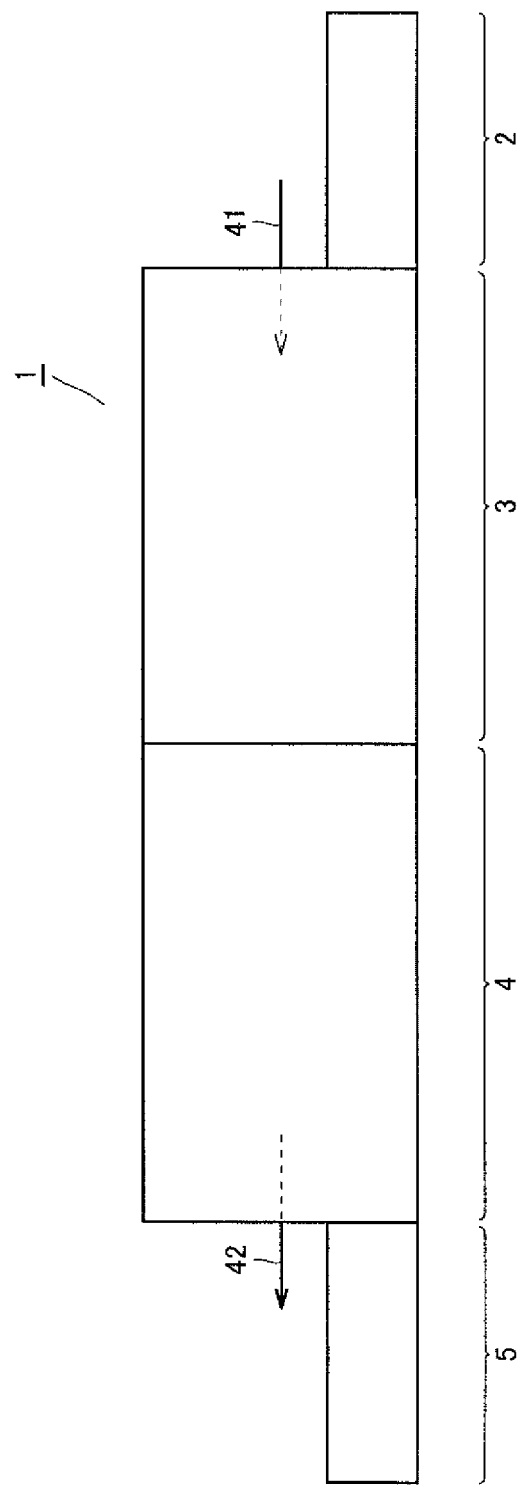
FIG. 1 is a side view schematically showing a configuration of a hatching egg inspection apparatus according to an embodiment of the present invention.

A hatching egg inspection apparatus according to an embodiment of the present invention will be described. As shown in FIG. 1, a hatching egg inspection apparatus 1 includes a loader unit 2 for receiving hatching eggs to be inspected, an inspection unit 3 for determining the viability or the like as to whether the hatching eggs received by loader unit 2 are an unfertilized egg or a growth-stopping egg, a rejection unit 4 for rejecting a hatching egg determined to be an unfertilized egg or the like in inspection unit 3, and an unloader unit 5 for sending, toward the next step, the hatching eggs after the unfertilized egg or the like is rejected. As described below, a plurality of hatching eggs to be inspected that are housed in a prescribed setter tray are sent from loader unit 2 to inspection unit 3 as shown by an arrow 41, and then, are sent through rejection unit 4 to unloader unit 5 as shown by an arrow 42.

Figure 2:
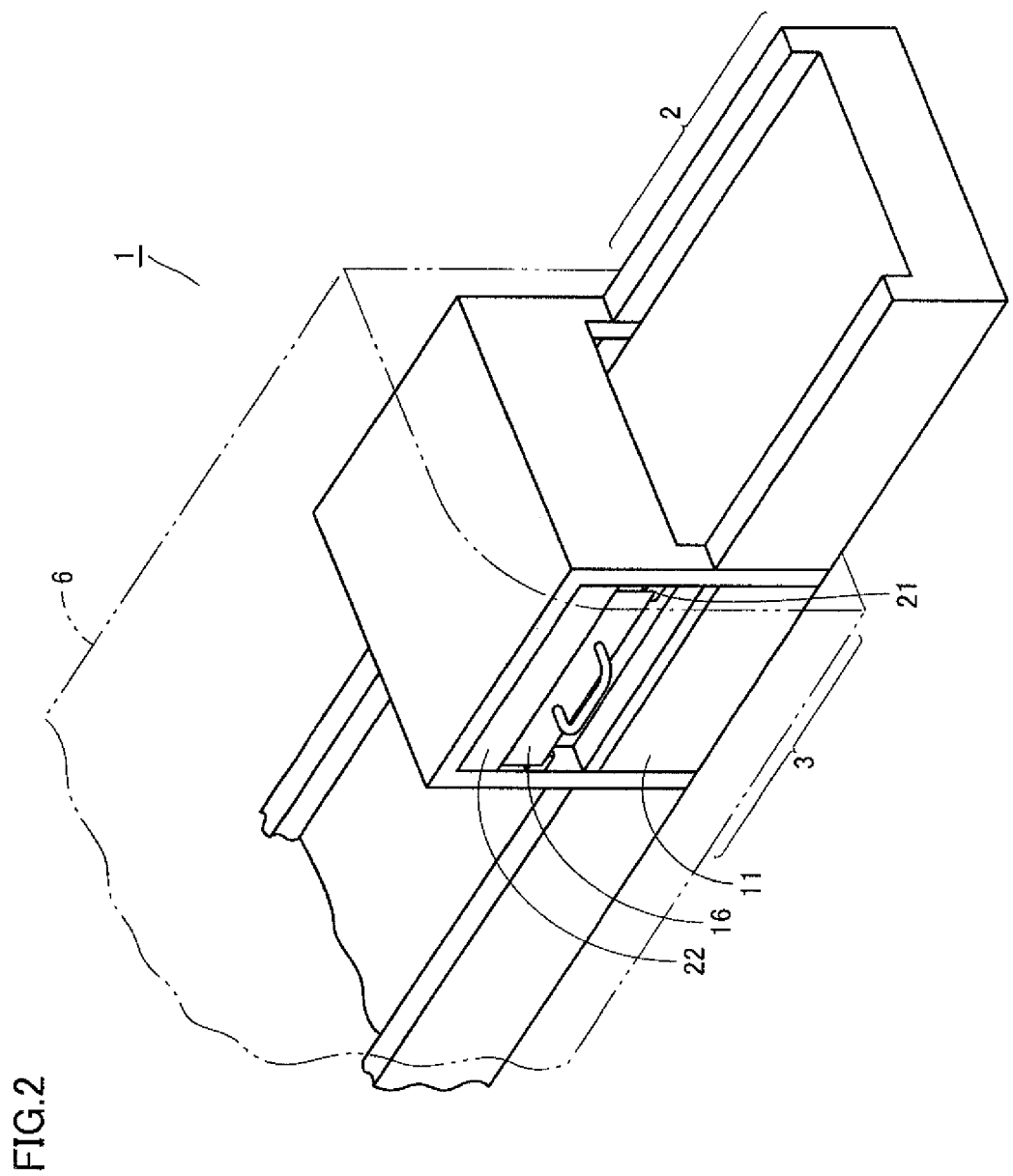
FIG. 2 is a partial perspective view showing a loader unit and an inspection unit in the hatching egg inspection apparatus in the embodiment.
Figure 3:
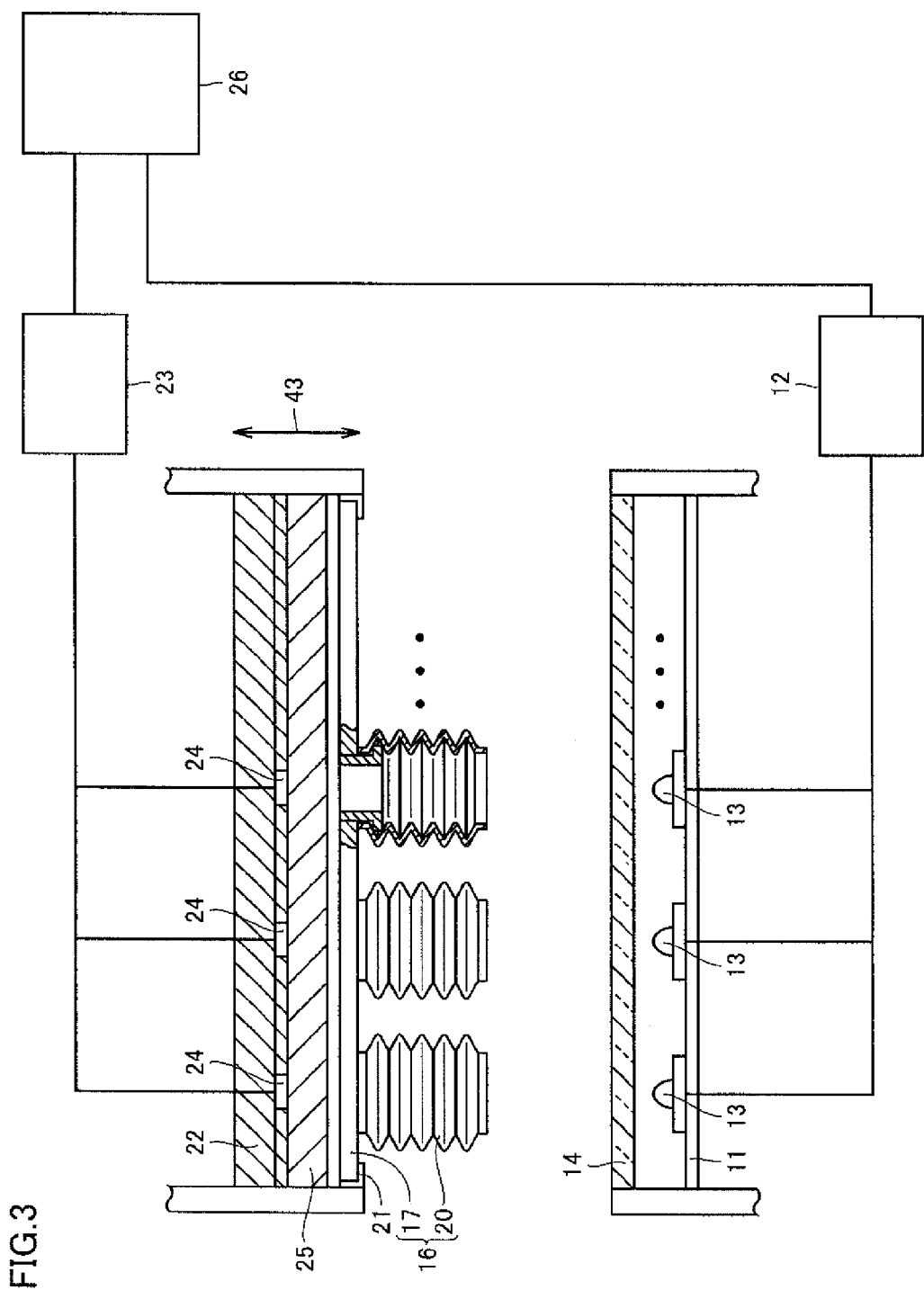
FIG. 3 is a side view including a partial cross section schematically showing a configuration of the inspection unit in the embodiment.

Next, inspection unit 3 for determining the viability or the like of the hatching eggs will be described in detail. As shown in FIGS. 2 and 3, inspection unit 3 is provided with a light emitting unit 11 for emitting the prescribed light toward the hatching eggs, a cap attachment unit 16 having attached thereto a cap 20 for allowing only the light having been emitted toward the hatching egg and having transmitted through the hatching egg to pass through, and a light receiving unit 22 for receiving the light that has passed through cap attachment unit 16. In the example shown in the figures, light emitting unit 11 is provided below an egg conveyance path shown by arrows 41 and 42, and cap attachment unit 16 is arranged above the conveyance path, and further, light receiving unit 22 is provided above cap attachment unit 16. Therefore, the light emitted from below by light emitting unit 11 passes through cap attachment unit 16 and is received by light receiving unit 22 provided above.

Figure 4:
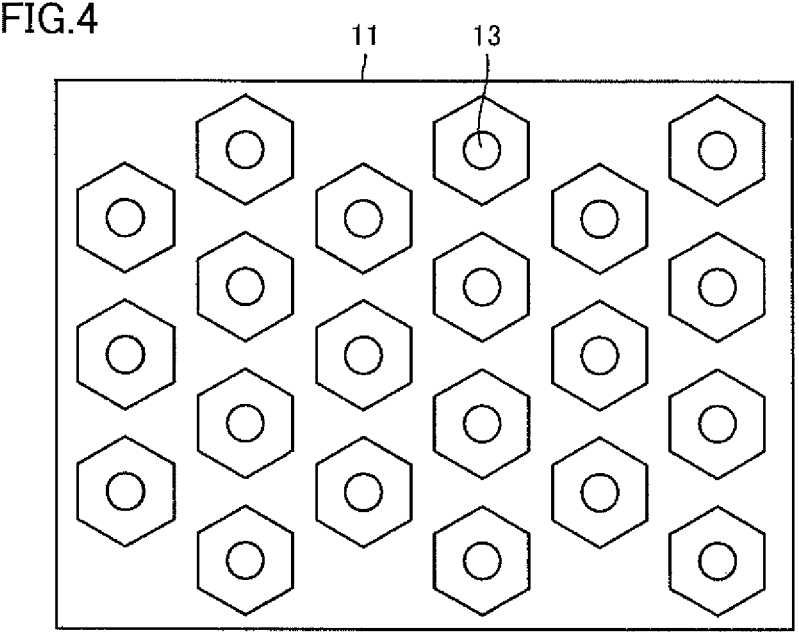
FIG. 4 is a plan view showing arrangement of light emitting elements of a light emitting unit in the embodiment.

As shown in FIG. 4, a plurality of light emitting elements 13 such as, for example, light emitting diodes are arranged in light emitting unit 11 to correspond to arrangement of the hatching eggs closely packed on the setter tray. The light emission intensity and the like of each of the plurality of light emitting elements 13 are adjusted by a light emission control unit 12 (see FIG. 3). As long as light emitting element 13 is an element that emits the light having a prescribed wavelength (region), light emitting element 13 is not limited to the light emitting diode and the laser light may, for example, be used. In addition, in the aforementioned inspection apparatus, light emitting elements 13 are provided to correspond to the plurality of hatching eggs, respectively. However, one light emitting element like a fluorescent lamp may be provided for the plurality of hatching eggs.

Figure 5:
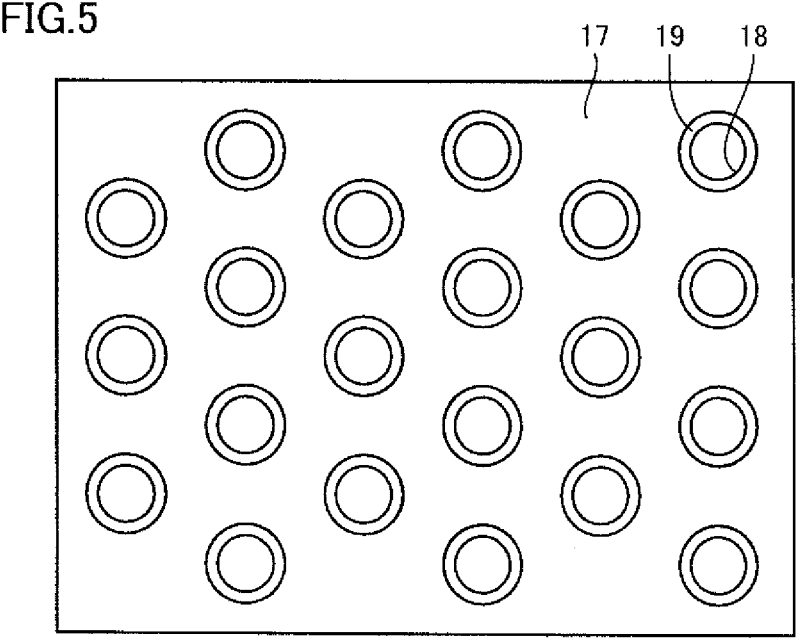
FIG. 5 is a plan view showing a base of a cap attachment unit in the embodiment.
Figure 6:
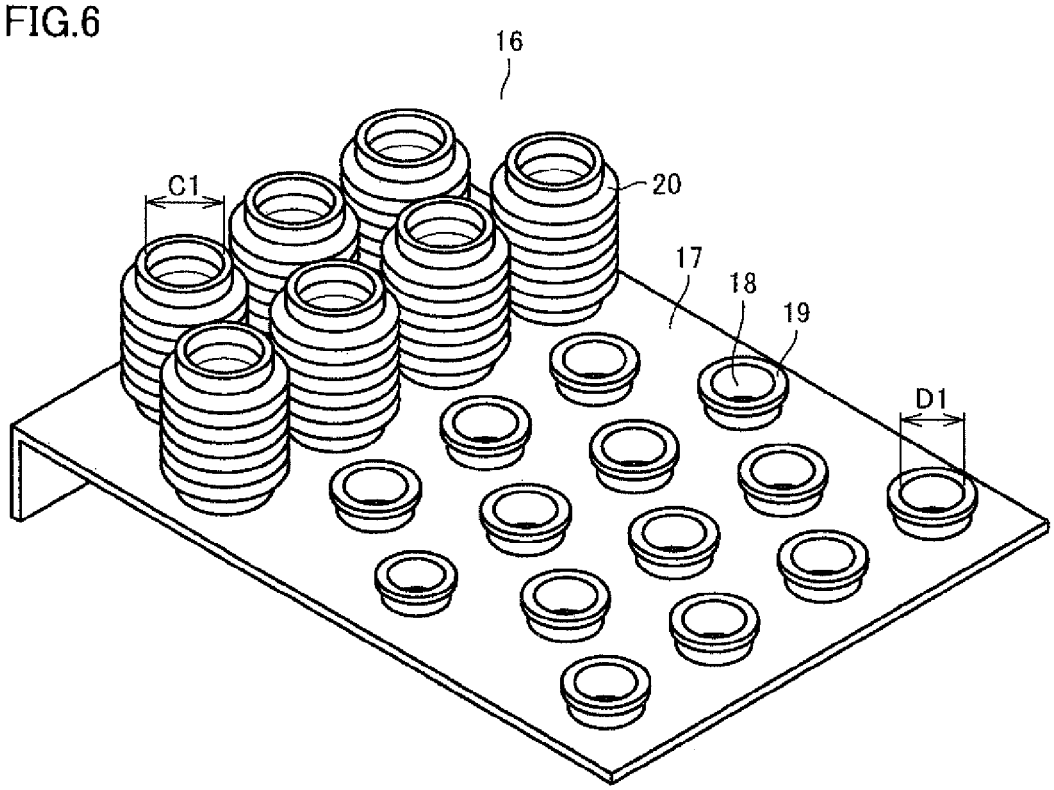
FIG. 6 is a perspective view showing a cap and the base of the cap attachment unit in the embodiment.

As shown in FIGS. 5 and 6, cap attachment unit 16 includes cylindrical cap 20 that comes into contact with the hatching egg, and a base to which cap 20 is attached, and cap attachment unit 16 is slidably held by a guide rail 21 (see FIG. 3). In the present embodiment, the base is a plate 17 formed in the shape of a plate. However, the base may have another shape to which cap 20 is attached. At the time of maintenance, cap attachment unit 16 is slid, and thereby, contaminated cap attachment unit 16 can be removed from inspection unit 3 and sterilized cap attachment unit 16 can be attached to inspection unit 3.

Each cap 20 includes a cylindrical member 201 having a side circumferential surface formed in the shape of bellows, and an annular member 202 that engages with cylindrical member 201. A plurality of annular members 202 are attached to or formed on plate 17. Cylindrical member 201 engages with each annular member 202, and thereby, a plurality of caps are attached to plate 17. As a result, during inspection, each of the plurality of caps 20 comes into contact with the corresponding hatching egg. In addition, with the aforementioned configuration, cap 20 can be removed independently of light receiving unit 22.

Figure 7:
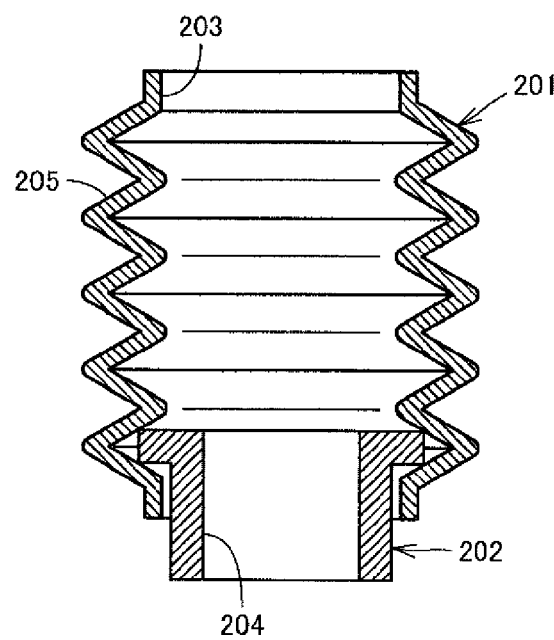
FIG. 7 is a sectional side view showing the cap in the embodiment.

As shown in FIG. 7, cap 20 includes a first opening portion 203 that comes into contact with the hatching egg, a second opening portion 204 spaced apart from first opening portion 203, and a connecting portion 205 interposed between first and second opening portions 203 and 204. First opening portion 203 is formed to come into close contact with an outer surface of the hatching egg, and is formed such that the light having transmitted through the inside of the hatching egg is incident through the outer surface of the hatching egg. Connecting portion 205 is formed such that the light incident from first opening portion 203 travels toward second opening portion 204, and is formed to expand and contract in the direction substantially vertical to first opening portion 203. Second opening portion 204 is formed such that the light having passed through connecting portion 205 exits toward light receiving unit 22.

First opening portion 203 is located at a bottom surface (in FIG. 7, an upper surface) of cylindrical member 201 of cap 20, and connecting portion 205 formed in the shape of bellows is located at the side circumferential surface of cylindrical member 201 of cap 20 continuous to first opening portion 203. Second opening portion 204 is located at a top surface (in FIG. 7, a lower surface) of annular member 202. First opening portion 203 has a circular opening so as to come into close contact with the hatching egg.

According to such cap 20, when cap 20 comes into contact with the hatching egg, connecting portion 205 contracts and first opening portion 203 reliably comes into close contact with the hatching egg. A plurality of hatching eggs are inspected simultaneously in inspection unit 3 and bellows-like connecting portion 205 can change the degree of contraction in accordance with the shape of the contacted hatching egg. Namely, connecting portion 205 contracts greatly for the hatching egg having a relatively large external dimension, and contracts a little for the hatching egg having a relatively small external dimension. As a result, first opening portion 203 of cap 20 corresponding to each of the plurality of hatching eggs can reliably come into close contact with the hatching egg.

Cap 20 may only be formed such that connecting portion 205 expands and contracts substantially vertically to first opening portion 203. Connecting portion 205 is not limited to the bellows-like shape and may be formed to have, for example, a telescopic structure.

In addition, cap 20 has a light blocking property such that only the light having been emitted from light emitting unit 11 and having transmitted through the hatching egg should be guided to light receiving unit 22, i.e., the other light should be blocked from light receiving unit 22. In order to provide the light blocking property to cap 20, a black-based coating material may, for example, be applied to an outer surface or an inner surface of the cap, or the cap may be fabricated from a light blocking material. The light blocking cap comes into close contact with the hatching egg during inspection, and thereby, only the light having transmitted through the hatching egg can be received by the light receiving element.

With such cap 20, each first opening portion 203 reliably comes into close contact with the corresponding hatching egg, without being affected by the external dimension of the hatching egg. As a result, with regard to all hatching eggs to be inspected, only the light having transmitted through each hatching egg, of the light emitted from light emitting unit 11, enters cap 20 from first opening portion 203, passes through the inside of cap 20 that blocks the light to the outside, and exits from second opening portion 204, and the light can be received by light receiving unit 22.

Since cap attachment unit 16 is cleaned with an antiseptic solution or the like after removal from the hatching egg inspection apparatus, cap 20 and plate 17 are desirably made of a chemical-resistant member. Particularly, cap 20 comes into direct contact with the shell of the hatching egg, and thus, a soft material such as, for example, chemical-resistant rubber is desirable. When cap 20 is made of a soft material such as rubber, attachment to and removal from an annular protruding portion 19 is easy, and thus, cleaning such as sterilization can be efficiently performed.

Figure 8:
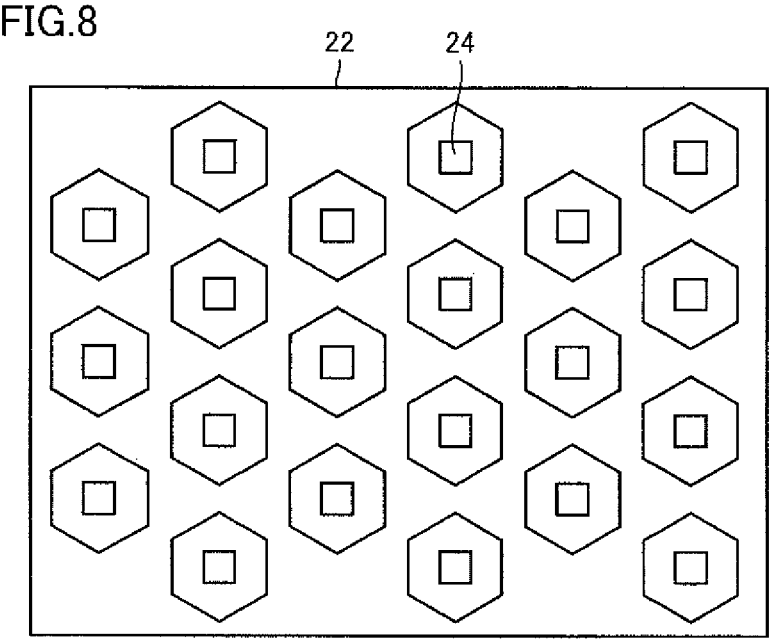
FIG. 8 is a plan view showing arrangement of light receiving elements of a light receiving unit in the embodiment.

As shown in FIG. 8, a plurality of light receiving elements 24 such as, for example, photodiodes are arranged in light receiving unit 22 to correspond to arrangement of the hatching eggs closely packed on the setter tray. The light received by the plurality of light receiving elements 24 travels through a photoelectric conversion unit 23 (see FIG. 3) as an electric signal, and a determination unit 26 determines the viability or the like as to whether the hatching egg to be measured is an unfertilized egg or a growth-stopping egg. In addition, the light reception sensitivity of each light receiving element 24 may be adjusted by photoelectric conversion unit 23. As long as light receiving element 24 can catch, as a signal, the prescribed light having transmitted through the hatching egg, light receiving element 24 is not limited to a photodiode.

Figure 9:
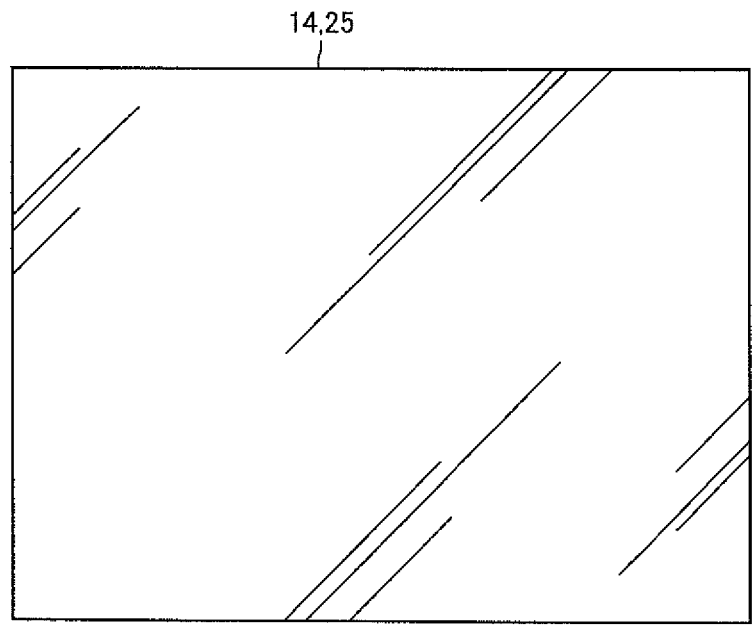
FIG. 9 is a plan view showing a light emitting unit protection plate or a light receiving unit protection plate in the embodiment.

As shown in FIGS. 3 and 9, a light emitting unit protection plate 14 for protecting light emitting unit 11 is attached between light emitting unit 11 and cap attachment unit 16, and a light receiving unit protection plate 25 for protecting light receiving unit 22 is attached between cap attachment unit 16 and light receiving unit 22. A glass plate is, for example, applicable as light emitting unit protection plate 14 and light receiving unit protection plate 25. In addition, light emitting unit protection plate 14 may be made of a material that allows the light having a particular wavelength range to transmit through based on the relationship with the wavelength of the light emitted by light emitting elements 13, and light receiving unit protection plate 25 may be made of a material that allows the light having a particular wavelength range to transmit through based on the relationship with the wavelength of the light component having transmitted through the hatching egg. As a result, the wavelength range of the light received by light receiving unit 22 is limited, and thus, the light detection sensitivity can be enhanced. Light receiving unit protection plate 25 may be adjustable for an amount of passing light, polarization of the light or the like by using liquid crystals, a polarizing plate or the like.

Figure 10:
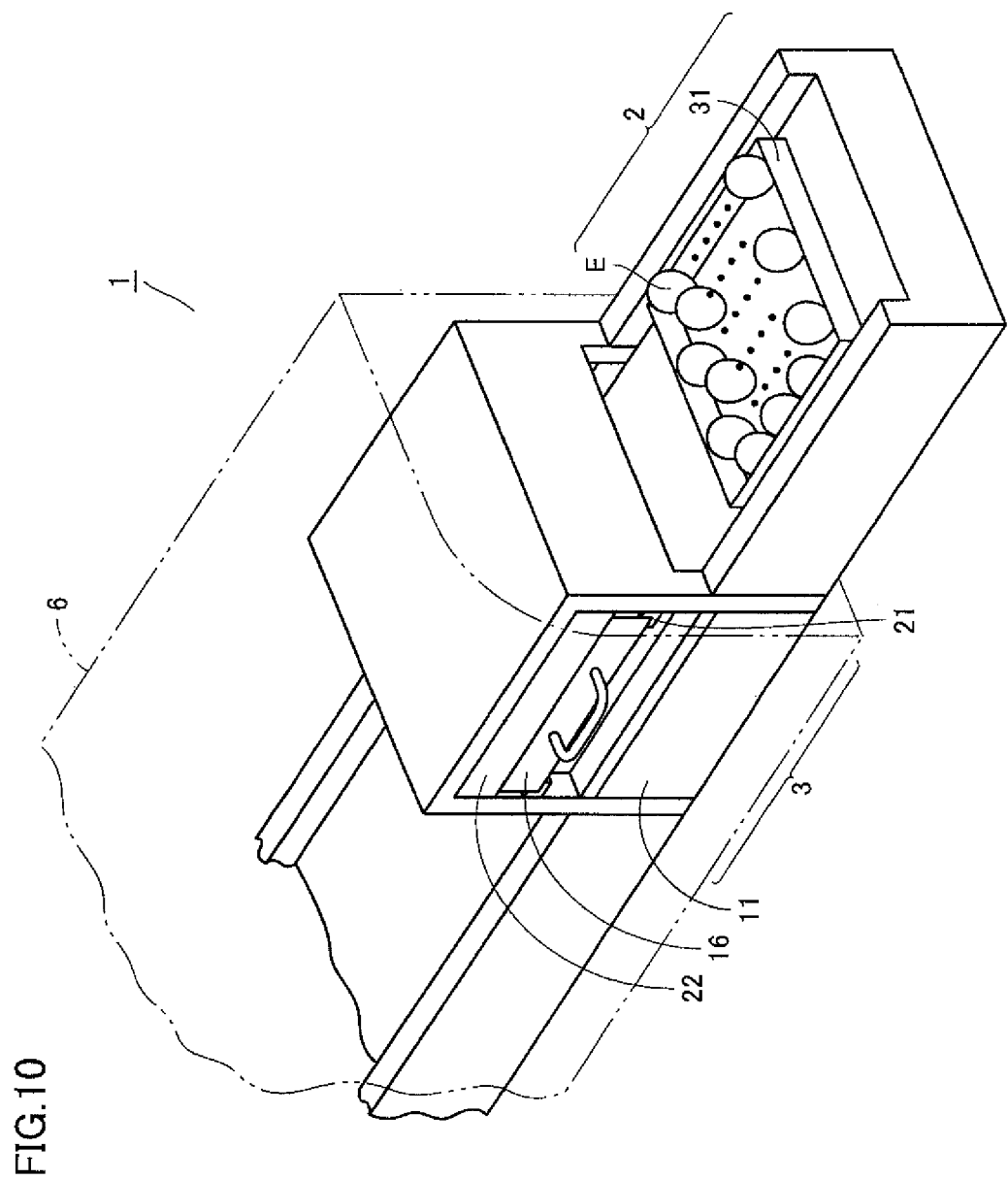
FIG. 10 is a partial perspective view showing a first state for describing inspection of hatching eggs by the hatching egg inspection apparatus in the embodiment.

Next, inspection of the hatching eggs by the aforementioned hatching egg inspection apparatus will be described. In the hatching egg inspection apparatus, the hatching eggs on day 18 or 19 of the number of incubation days, which will hatch two or three days after, are mainly subjected to inspection. In the hatchery where a large number of chicks are hatched, batch processing for simultaneously inspecting the prescribed number of hatching eggs is performed to ensure the productivity. Therefore, as shown in FIG. 10, a plurality of hatching eggs E to be inspected are first closely packed on a setter tray 31 and are loaded into loader unit 2 of hatching egg inspection apparatus 1.

Figure 11:
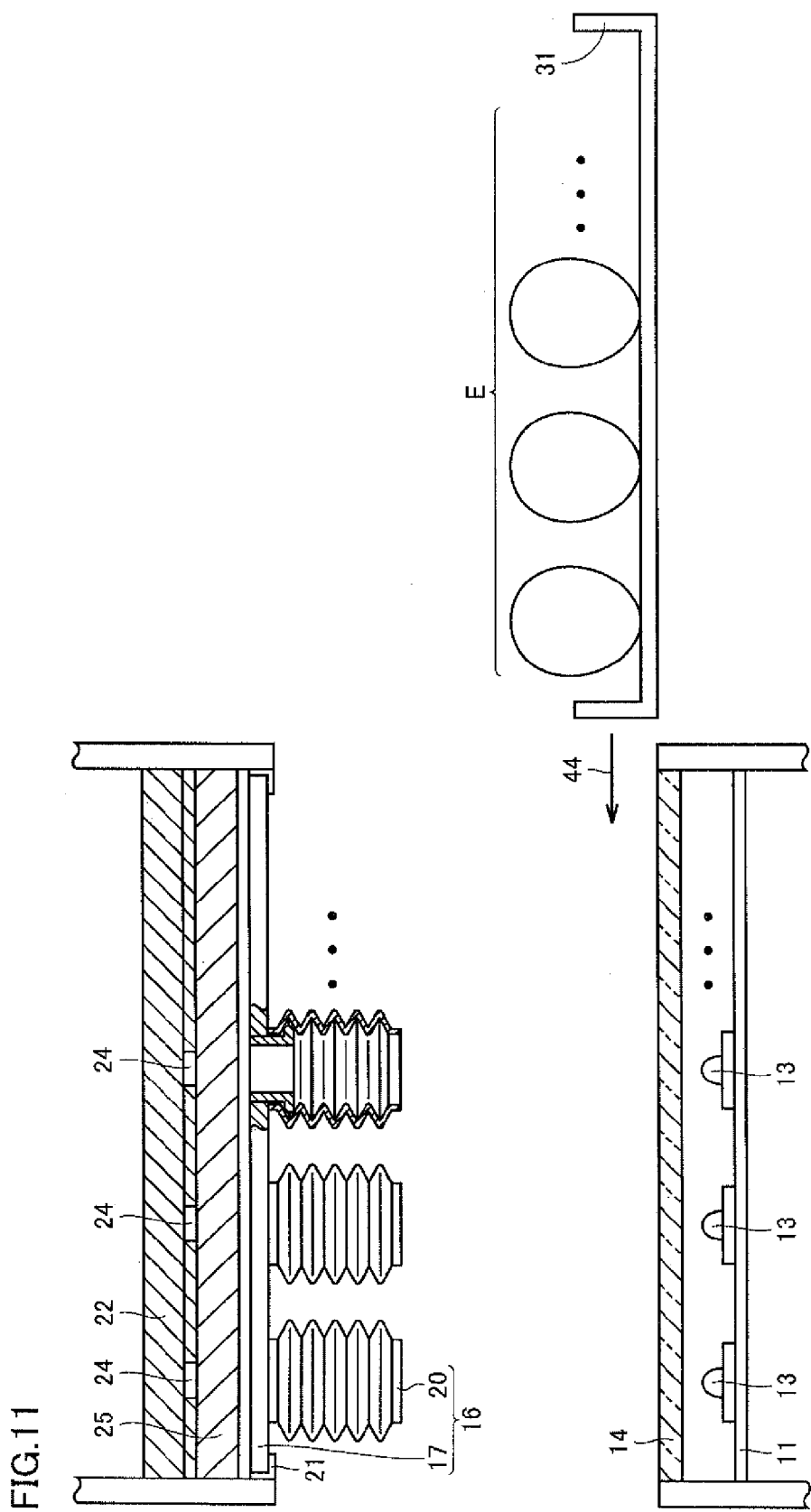
FIG. 11 is a partial side view including a partial cross section showing a second state for describing inspection of the hatching eggs by the hatching egg inspection apparatus in the embodiment.
Figure 12:
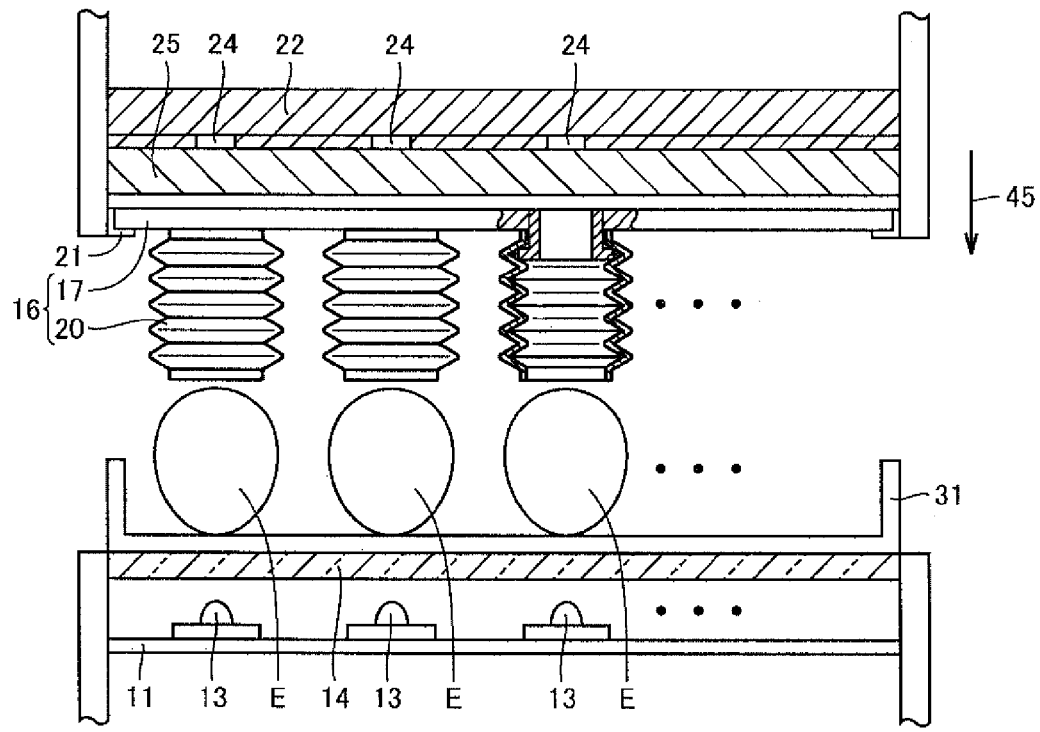
FIG. 12 is a partial side view including a partial cross section showing a third state for describing inspection of the hatching eggs by the hatching egg inspection apparatus in the embodiment.
Figure 13:
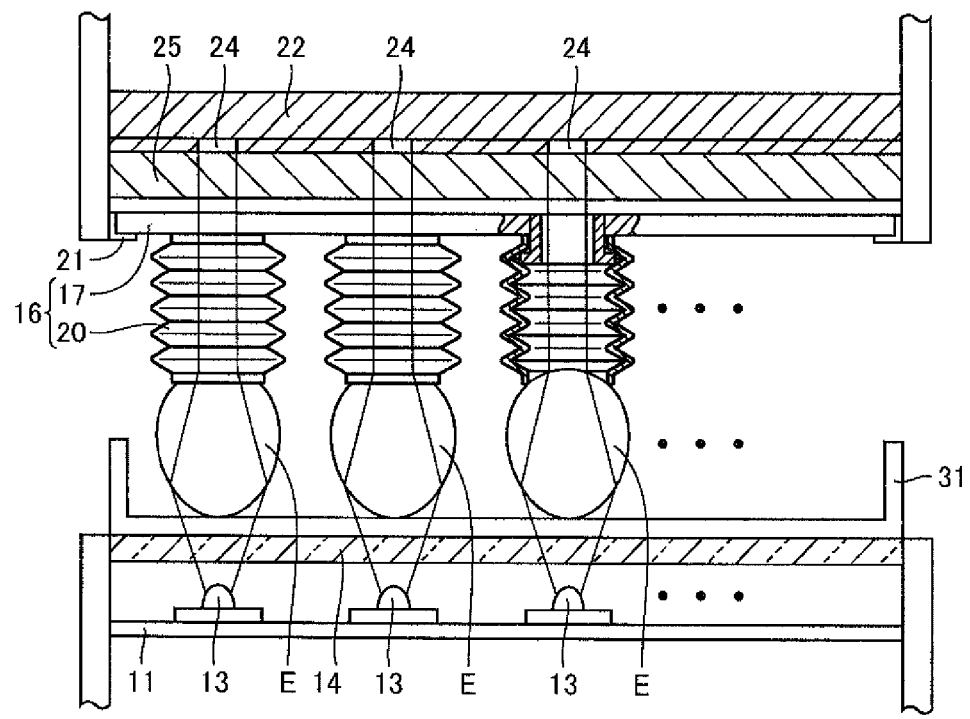
FIG. 13 is a partial side view including a partial cross section showing a fourth state for describing inspection of the hatching eggs by the hatching egg inspection apparatus in the embodiment.

As shown in FIG. 11, hatching eggs E loaded into loader unit 2 is conveyed toward a position between light emitting unit 11 and cap attachment unit 16 as shown by an arrow 44, with hatching eggs E placed on setter tray 31. As shown in FIG. 12, when setter tray 31 reaches the prescribed position between light emitting unit 11 and cap attachment unit 16, setter tray 31 stops at that position. Next, with setter tray 31 being at the prescribed position, cap attachment unit 16 moves downward as shown by an arrow 45. As a result of the downward movement of cap attachment unit 16, each of the plurality of caps 20 arranged to correspond to arrangement of the hatching eggs closely packed on setter tray 31 comes into contact with corresponding hatching egg E as shown in FIG. 13. At this time, first opening portion 203 of cap 20 reliably comes into close contact with corresponding hatching egg E because the side circumferential surface of cap 20 has a bellows-like shape.

Next, the light having a prescribed intensity is emitted from each of the plurality of light emitting elements 13 of light emitting unit 11 toward corresponding hatching egg E for approximately several seconds, for example. A part of the light emitted toward hatching egg E transmits through hatching egg E and passes through cap 20 that is in contact with the shell of hatching egg E. The light having passed through cap 20 is received by corresponding light receiving element 24. The light received by light receiving element 24 is sent as an electric signal to determination unit 26 through photoelectric conversion unit 23.

Figure 14:
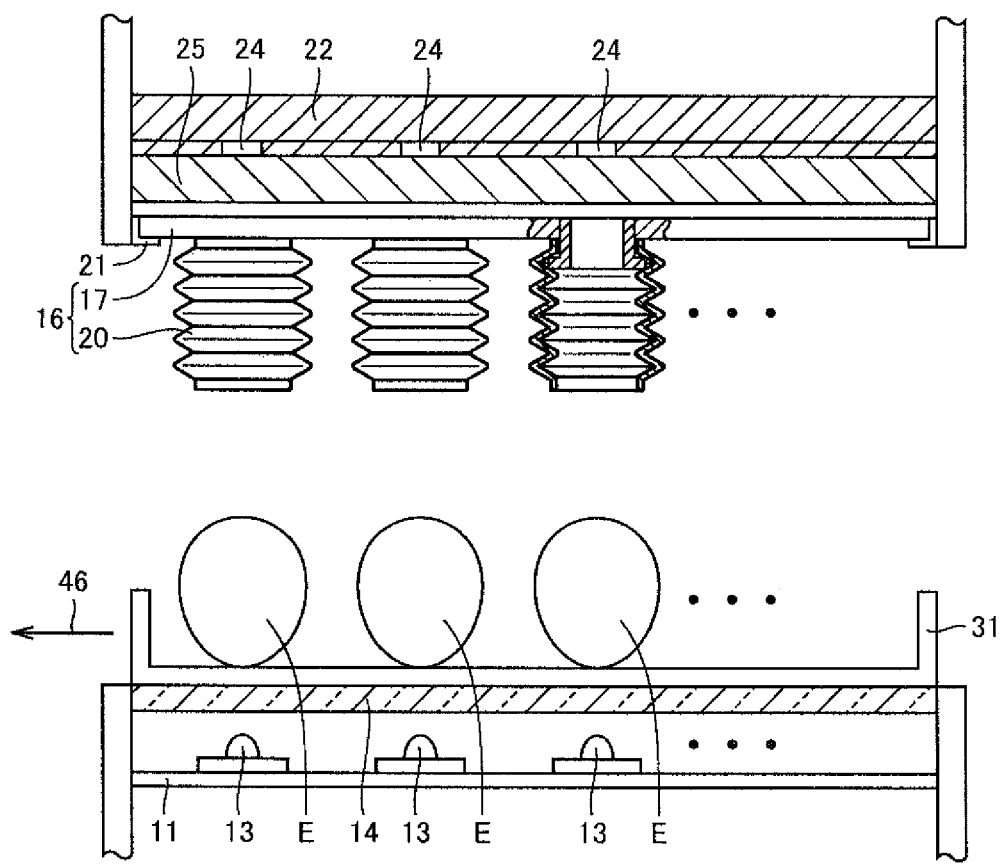
FIG. 14 is a partial side view including a partial cross section showing a fifth state for describing inspection of the hatching eggs by the hatching egg inspection apparatus in the embodiment.

Determination unit 26 makes a comparison with the preliminarily obtained data, and thereby, determines whether hatching egg E to be measured is an unfertilized egg or a growth-stopping egg. In this hatching egg inspection apparatus 1, the viability of hatching egg E is determined by particularly reading a signal (vital sign) about a heartbeat or a fetal movement of an embryo in hatching egg E, in addition to the intensity of the light having transmitted through hatching egg E. The result of determination is stored together with the identification information of setter tray 31 and the positional information of hatching egg E. When the inspection ends, cap attachment unit 16 moves upward to a prescribed position and setter tray 31 that houses the hatching eggs is conveyed to rejection unit 4 (see FIG. 1) as shown in FIG. 14.

Rejection unit 4 rejects the hatching egg determined to be an unfertilized egg or a growth-stopping egg from the setter tray, based on the result of determination, the identification information of setter tray 31 and the positional information of hatching egg E. The setter tray that houses only the healthily grown hatching eggs as a result of the rejection of the unfertilized egg or the growth-stopping egg is conveyed to unloader unit 5 (see FIG. 1) and is sent from unloader unit 5 toward the next step. A series of inspection of the plurality of hatching eggs E housed in setter tray 31 is thus completed.

Generally, in order to hatch healthy and tough chicks, it is necessary to prevent contamination of the hatching eggs and to prevent spreading of contamination, and it is required to constantly keep the environment for hatching the hatching eggs hygienic. Without exception, the hatching egg inspection apparatus must be kept hygienic. Particularly in the hatching egg inspection apparatus in the hatchery where a large number of chicks are hatched, the setter tray that houses the plurality of hatching eggs is loaded one after another, and for each loaded setter tray, the plurality of hatching eggs are simultaneously inspected to determine the viability of the hatching eggs, in order to ensure the productivity. Therefore, in order to prevent spreading of contamination into the healthy hatching eggs caused by contact of cap 20 with the hatching eggs sent one after another, cap attachment unit 16 requires routine maintenance such as sterilization.

Figure 15:
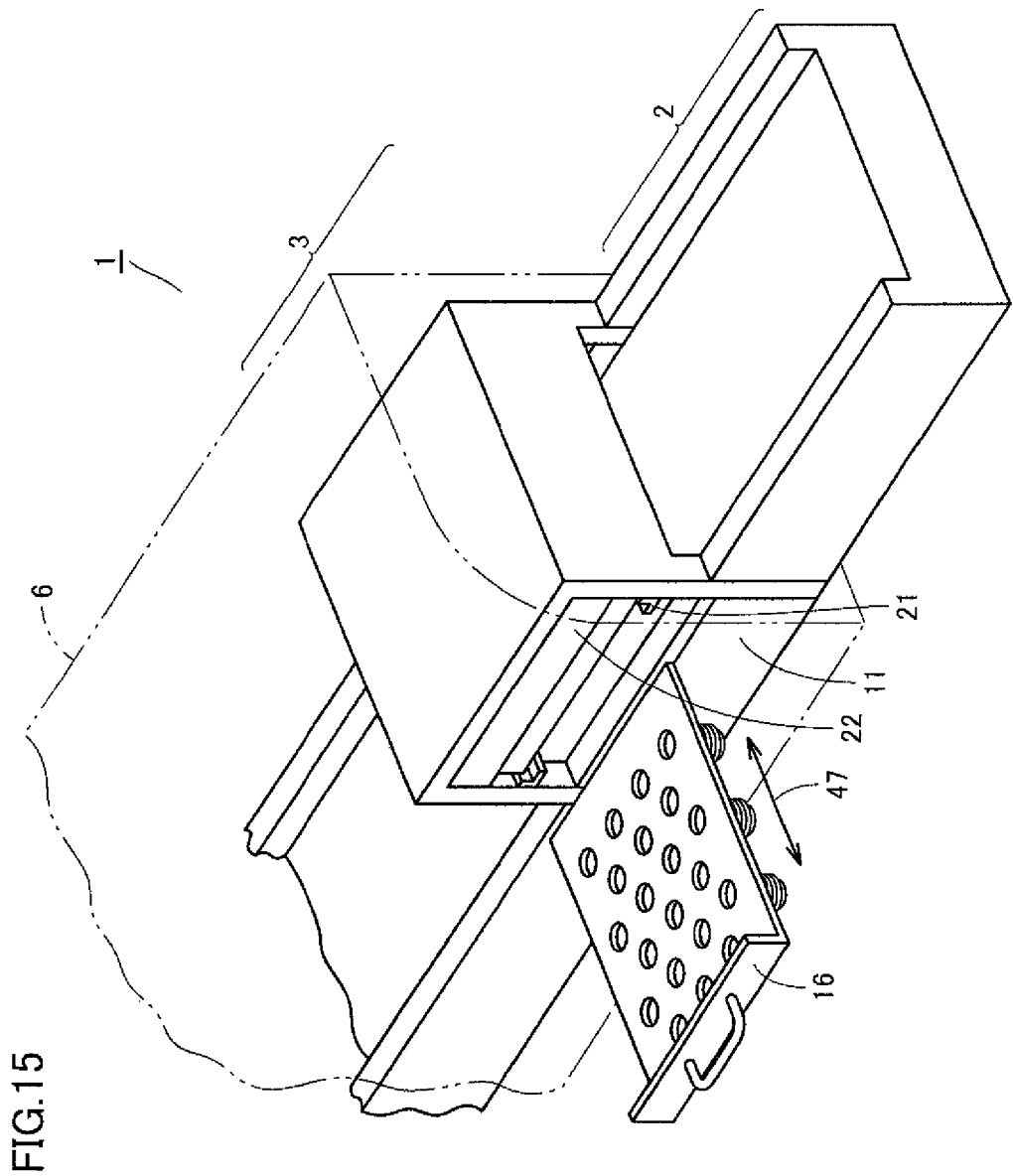
FIG. 15 is a first partial perspective view for describing a characteristic of the cap attachment unit in the inspection unit in the embodiment.

In hatching egg inspection apparatus 1 described above, cap attachment unit 16 is slidably held by guide rail 21. Namely, in the example shown in the figures, guide rail 21 functions as a holding unit. As a result, as shown in FIG. 15, at the time of maintenance, cap attachment unit 16 is slid (arrow 47), and thereby, cap attachment unit 16 can be easily removed from inspection unit 3 to perform sterilization or the like. When maintenance such as sterilization is completed, cap attachment unit 16 is slid (arrow 47), and thereby, cap attachment unit 16 can be easily attached to inspection unit 3, and thus, measures can be easily taken against contamination for cap attachment unit 16.

Figure 16:
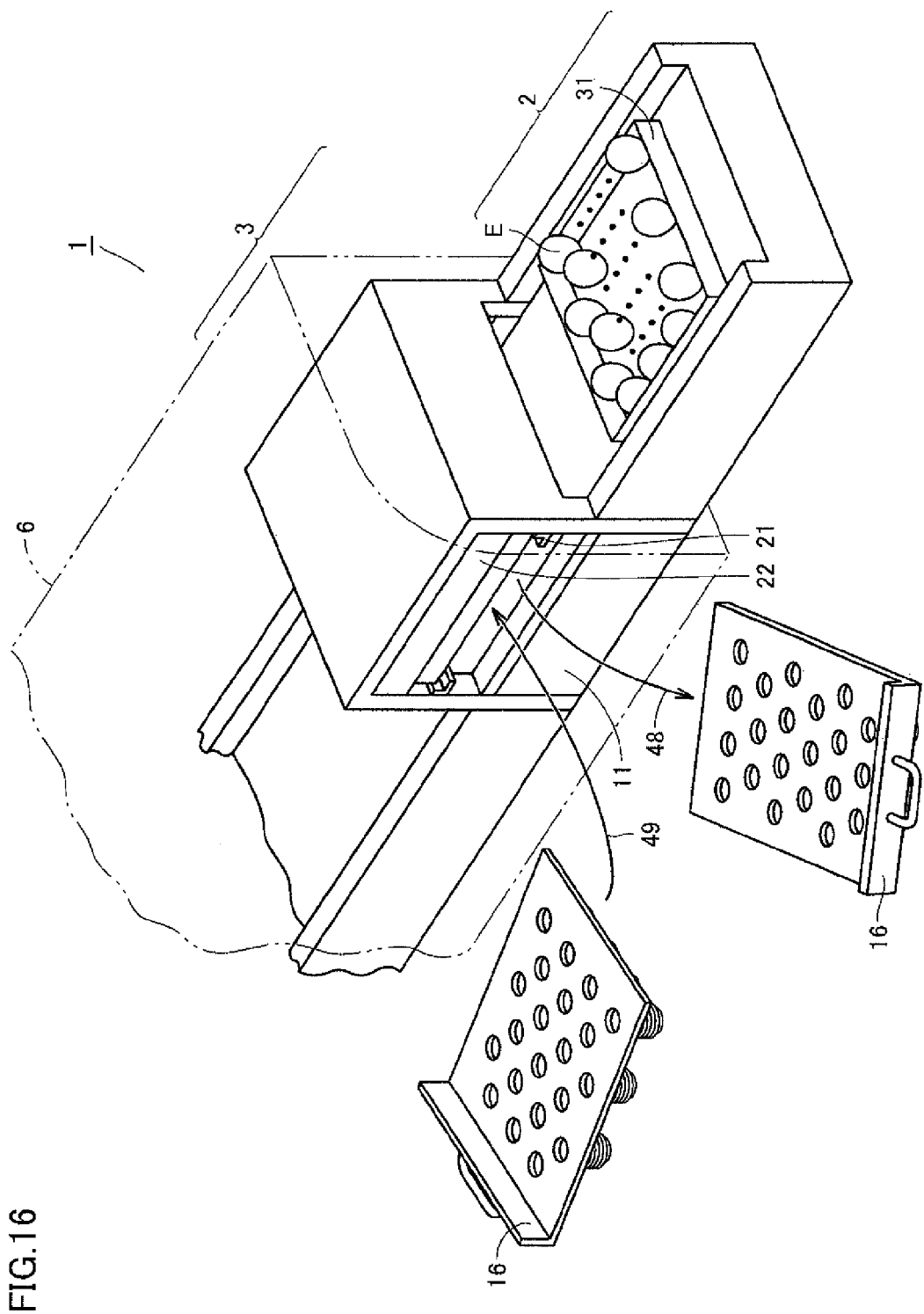
FIG. 16 is a second partial perspective view for describing a characteristic of the cap attachment unit in the inspection unit in the embodiment.

By preliminarily preparing a plurality of sterilized cap attachment units and replacing cap attachment unit 16 with the sterilized cap attachment unit 16 at the time of maintenance as shown in FIG. 16, maintenance can be performed almost without hampering the productivity. Particularly, even when "explosion egg" called by the inventors explodes actually due to contact with cap 20 or the like, and miscellaneous bacteria or the like attach to the plurality of caps 20 or the like, replacing cap attachment unit 16 with sterilized cap attachment unit 16 makes it possible to reliably suppress spreading of the miscellaneous bacteria into the other healthy hatching eggs almost without hampering the productivity.

It is assumed that the rotten contents including the miscellaneous bacteria are scattered from an opening 18 of cap attachment unit 16 to light receiving unit 22 due to the explosion of the explosion egg. In this hatching egg inspection apparatus, light receiving unit protection plate 25 is provided between cap attachment unit 16 and light receiving unit 22. Therefore, the scattered contents attach to light receiving unit protection plate 25 and contamination of light receiving unit 22 can be prevented. Moreover, the contents attached to light receiving unit protection plate 25 can be easily removed by cleaning, sterilization and the like with cap attachment unit 16 removed and light receiving unit protection plate 25 exposed as shown in FIG. 16 (see arrows).

On the other hand, it is also assumed that the rotten contents including the miscellaneous bacteria fall onto light emitting unit 11 due to the explosion of the explosion egg. In this hatching egg inspection apparatus, light emitting unit protection plate 14 is provided between cap attachment unit 16 and light emitting unit 11. Therefore, the fallen contents attach to light emitting unit protection plate 14 and contamination of light emitting unit 11 can be prevented. Moreover, the contents attached to light emitting unit protection plate 14 can be easily removed by cleaning, sterilization and the like with light emitting unit protection plate 14 and light receiving unit protection plate 25 exposed as shown in FIG. 17 (see arrows).

As described above, in the aforementioned hatching egg inspection apparatus, as the measures against contamination for the cap attachment unit that comes into contact with the hatching eggs, the cap attachment unit is detachably held by the guide rail, and thus, the contaminated cap attachment unit can be easily replaced with the sterilized cap attachment unit. As a result, contamination of the hatching egg inspection apparatus can be prevented and spreading of contamination can be stopped without hampering the productivity. Particularly, even in the case where the explosion egg explodes and the contents including the miscellaneous bacteria attach to the cap attachment unit, the cap attachment unit is slid such that the contaminated cap attachment unit can be easily replaced with the sterilized cap attachment unit. As a result, spreading of contamination can be stopped without hampering the productivity.

In the aforementioned hatching egg inspection apparatus, a mechanism held by the guide rail has been described by way of example as a mechanism for detachably holding the cap attachment unit. However, as long as the mechanism can detachably hold the cap attachment unit, the mechanism is not limited thereto. For example, a crimp-type mechanism using a clamp or the like, a mechanism using a magnet, or the like may be used. In addition, the chicken egg has been described by way of example as the hatching egg to be inspected. However, the hatching egg is not limited to the chicken egg, and a hatching egg of a duck, a turkey, a quail or the like can, for example, be subjected to inspection.

Figure 18:
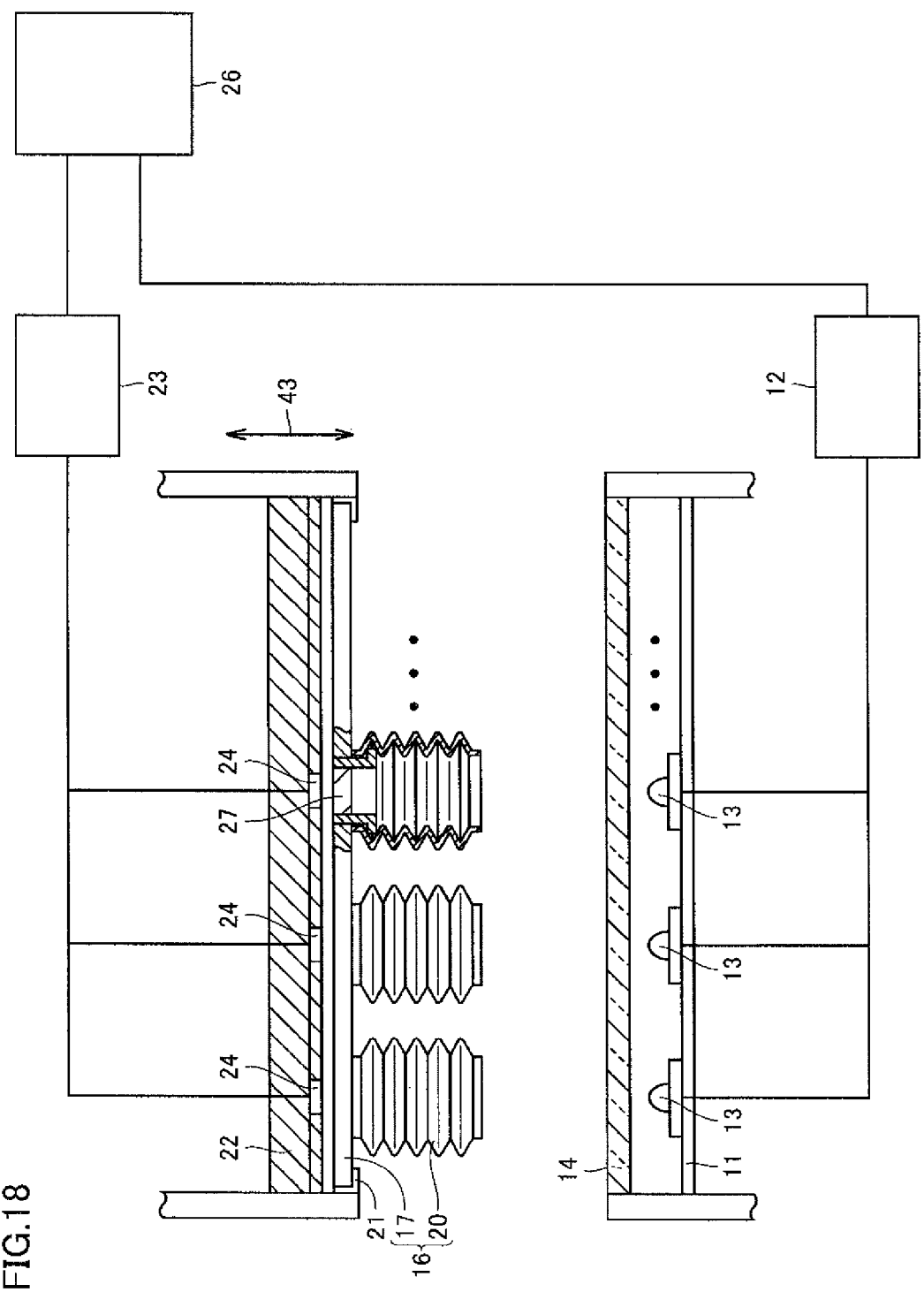
FIG. 18 is a side view including a partial cross section schematically showing a configuration of an inspection unit in a hatching egg inspection apparatus according to a modification in the embodiment.

Furthermore, description has been given by way of example to the structure in which the light receiving unit protection plate is arranged between the cap attachment unit and the light receiving unit. However, instead of arranging the light receiving unit protection plate between the cap attachment unit and the light receiving unit, a light receiving unit protection plate 27 may be arranged in an opening of plate 17 of cap attachment unit 16 as shown in FIG. 18. In this case, when cleaning and the like of cap attachment unit 16 is performed, cleaning and the like of light receiving unit protection plate 27 can also be performed simultaneously. In addition, cap attachment unit 16 and light receiving unit protection plate 25 may be configured to be simultaneously removed together.

Furthermore, description has been given by way of example to the case of inspecting the hatching eggs on day 18 or 19 of the number of incubation days in the aforementioned inspection. As for the aforementioned hatching eggs immediately before hatching, the light is difficult to transmit through or diffuse in the eggs. Therefore, in inspection unit 3, the light emission intensity of light emitting unit 11 and the light reception sensitivity of light receiving unit 22 are adjusted to deal with such a situation.

Figure 19:
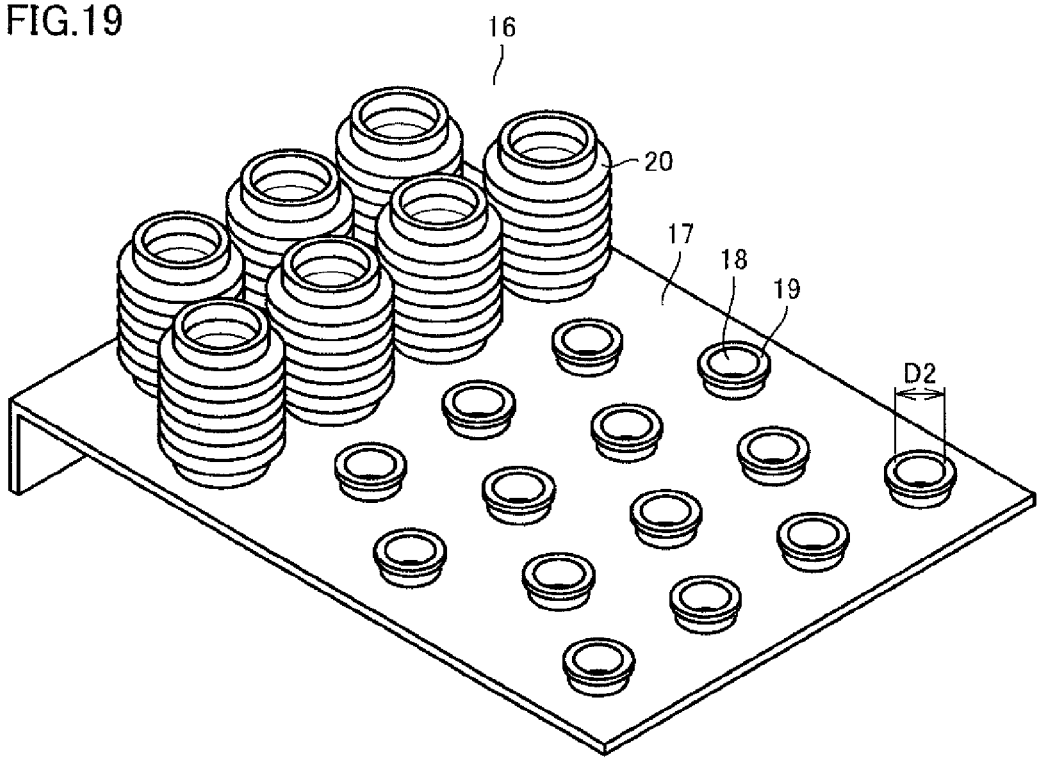
FIG. 19 is a perspective view showing a cap and a base of a cap attachment unit in the hatching egg inspection apparatus according to the modification in the embodiment.

However, when an attempt is, for example, made to inspect the hatching eggs on around day 10 of the number of incubation days under this condition, the accuracy of determining the viability of the hatching eggs may deteriorate because the light emission intensity is too high. Thus, in addition to the plate having opening 18 of an opening diameter D1 as shown in FIG. 6, it is desirable to include, as a plate of the cap attachment unit, a plate having opening 18 of an opening diameter D2 smaller than opening diameter D1 in order to limit an amount of light received by the light receiving unit as shown in FIG. 19. By replacement with the cap attachment unit including the plate having the opening of smaller opening diameter, the viability of the aforementioned hatching eggs with the smaller number of incubation days can also be determined without deterioration of the accuracy. Therefore, inspection is not limited to the hatching eggs with the particular number of incubation days, and it becomes possible to accurately inspect the hatching eggs with the arbitrary number of incubation days.

Figure 20:
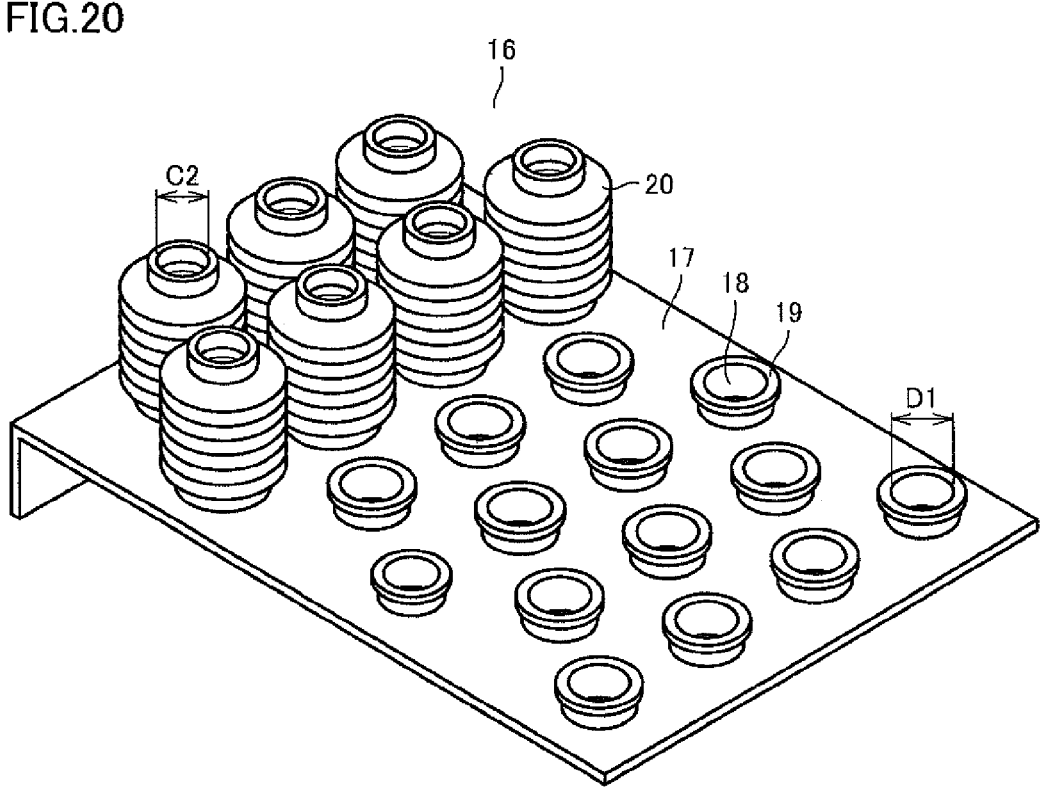
FIG. 20 is a perspective view showing a cap and a base of a cap attachment unit in a hatching egg inspection apparatus according to another modification in the embodiment.

Instead of using the cap attachment unit including the plate different in opening diameter of the opening, a cap attachment unit having attached thereto a cap different in cap opening diameter of the cap may be used. Namely, in addition to the cap of a cap opening diameter C1 as shown in FIG. 6, cap attachment unit 16 having attached thereto cap 20 of a cap opening diameter C2 smaller than cap opening diameter C1 as the cap opening diameter of the cap opening located on the side coming into contact with the hatching egg may be used as shown in FIG. 20. In this case as well, the viability of the hatching eggs with the smaller number of incubation days can be determined without deterioration of the accuracy.

Furthermore, when the cap attachment units including the openings of the plates different in opening diameter and the caps different in cap opening diameter are prepared, it is preferable that the hatching egg inspection apparatus recognizes which type of cap attachment unit is currently attached to the inspection unit. For example, a protrusion or the like recognized by a sensor can be provided on the plate to recognize the type of the cap attachment unit attached to the inspection unit. This is checked on a display or the like of the hatching egg inspection apparatus, and thereby, it is possible to prevent the hatching eggs from being inspected in the state where the cap attachment unit not corresponding to the number of incubation days is attached.

In the present invention, the side circumferential surface of the cap contracts such that the cap can come into close contact with egg E serving as the hatching egg to be inspected. As a result, a distance from the outer shell of the egg through which the light passes to the light receiving unit varies from egg to egg due to an individual difference of each egg. In the present embodiment, however, a set of the light emitting elements, the cap and the light receiving unit function for each hatching egg at the time of inspection. As a result, the light emission intensity of the light emitting elements or the light reception sensitivity of the light receiving unit can be adjusted for each hatching egg by the light irradiation unit control unit or the light receiving unit control unit. Therefore, even when the distance from the outer shell of the hatching egg to the light receiving unit changes, the light intensity or the light reception sensitivity is adjusted for each hatching egg, and thus, inspection can be performed without being affected by the distance from the outer shell of the hatching egg to the light receiving unit.

The embodiment disclosed herein is illustrative and not limitative in any respect. The present invention is defined by the terms of the claims, rather than the description above, and is intended to include any modifications within the scope and meaning equivalent to the terms of the claims.

INDUSTRIAL APPLICABILITY

The present invention is effectively used for incubation of eggs of poultry.

REFERENCE SIGNS LIST 1 hatching egg inspection apparatus; 2 loader unit; 3 inspection unit; 4 rejection unit; 5 unloader unit; 6 cover; 11 light emitting unit; 12 light emission control unit; 13 light emitting element; 14 light emitting unit protection plate; 16 cap attachment unit; 17 plate; 18 opening; 19 annular protruding portion; 20 cap; 21 guide rail; 22 light receiving unit; 23 photoelectric conversion unit; 24 light receiving element; 25 light receiving unit protection plate; 26 determination unit; 27 light receiving unit protection plate; 31 setter tray; E hatching egg; 41 to 49 arrow; 201 cylindrical member; 202 annular member; 203 first opening portion; 204 second opening portion; 205 connecting portion.

The invention claimed is:

1. A hatching egg inspection apparatus for inspecting a plurality of hatching eggs each arranged at a prescribed position, comprising:
    a light emitting unit including a light emitting element arranged to correspond to said prescribed position and emitting prescribed light from said light emitting element toward each corresponding hatching egg;
    a cap attachment unit having: a cap which is arranged to correspond to said prescribed position, which comes into contact with said hatching egg, and which allows the light having been emitted from said light emitting element and having transmitted through the inside of or diffused in said hatching egg to pass through; and a base to which said cap is attached;
    a light receiving unit including a light receiving element for receiving the light that has passed through said cap attachment unit via said cap; and
    a holding unit for detachably holding said cap attachment unit, wherein
    said cap includes a first opening portion coming into contact with said hatching egg, a second opening portion spaced apart from said first opening portion, and a connecting portion interposed between said first and second opening portions,
    said first opening portion is formed to come into close contact with an outer surface of said hatching egg, and is formed such that the light having transmitted through the inside of said hatching egg is incident through the outer surface of said hatching egg,
    said connecting portion is formed such that the light incident from said first opening portion travels toward said second opening portion, and is formed to expand and contract in a direction substantially vertical to said first opening portion, and
    said second opening portion is formed such that the light having passed through said connecting portion exits toward said light receiving unit.

2. The hatching egg inspection apparatus according to claim 1, further comprising
    a light receiving unit protection unit arranged between said cap attachment unit and said light receiving unit to protect said light receiving unit, said light receiving unit protection unit being made of a material that allows the light of a particular wavelength range associated with the light emitted by said light emitting unit to transmit through.

3. The hatching egg inspection apparatus according to claim 1, further comprising
    a light receiving unit protection unit arranged between said cap attachment unit and said light receiving unit to protect said light receiving unit, said light receiving unit protection unit being detachable together with said cap attachment unit.

4. The hatching egg inspection apparatus according to claim 1, wherein a light emission intensity of each said light emitting element is adjusted.

5. The hatching egg inspection apparatus according to claim 1, further comprising a light emitting unit protection unit arranged between said cap attachment unit and said light emitting unit to protect said light emitting unit.

6. The hatching egg inspection apparatus according to claim 1, wherein said cap attachment unit includes:

a first cap attachment unit having a first base to which a plurality of said caps each having said first opening portion of a first opening diameter are attached; and a second cap attachment unit having a second base to which a plurality of said caps each having said first opening portion of a second opening diameter are attached.

7. The hatching egg inspection apparatus according to claim 1, wherein said cap attachment unit includes:

a third cap attachment unit to which a first cap is attached, said first cap having a first cap opening diameter as a cap opening diameter of a cap opening of said cap located on a side coming into contact with said hatching egg; and a fourth cap attachment unit to which a second cap is attached, said second cap having a second cap opening diameter different from said first cap opening diameter as said cap opening diameter.

8. A hatching egg inspection apparatus for inspecting a plurality of hatching eggs that allow light to transmit through, with said hatching eggs each arranged at a prescribed position, comprising:

a light irradiation unit for emitting the light toward said hatching eggs;

a plurality of light passing units each of which is arranged to correspond to said prescribed position, which allows only the light having transmitted through the inside of said hatching egg, of the light emitted from said light irradiation unit, to pass through, and which blocks the passing light from the other light; and a light receiving unit spaced apart from said light passing units and receiving the light having passed through each light passing unit, wherein each light passing unit includes a cap that comes into contact with said hatching egg and can be separated from said light receiving unit, said cap includes a first opening portion coming into contact with said hatching egg, a second opening portion spaced apart from said first opening portion, and a connecting portion interposed between said first and second opening portions, said first opening portion is formed to come into close contact with an outer surface of said hatching egg, and is formed such that the light having transmitted through the inside of said hatching egg is incident through the outer surface of said hatching egg, said connecting portion is formed such that the light incident from said first opening portion travels toward said second opening portion and is formed to expand and contract in a direction substantially vertical to said first opening portion, and said second opening portion is formed such that the light having passed through said connecting portion exits toward said light receiving unit.

9. The hatching egg inspection apparatus according to claim 8, wherein said connecting portion is formed in a shape of bellows to expand and contract in a direction substantially vertical to said first opening portion.

\* \* \* \* \*